United States Patent
Heinlein

(10) Patent No.: US 11,577,893 B2
(45) Date of Patent: Feb. 14, 2023

(54) VIAL STOPPER FOR A LYOPHILIZATION VIAL AND CLOSURE METHOD FOR CLOSING A LYOPHILIZATION VIAL

(71) Applicant: Hoffmann-La Roche Inc., Little Falls, NJ (US)

(72) Inventor: Harald Heinlein, Mannheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 280 days.

(21) Appl. No.: 16/831,161

(22) Filed: Mar. 26, 2020

(65) Prior Publication Data

US 2020/0223604 A1 Jul. 16, 2020

Related U.S. Application Data

(63) Continuation of application No. PCT/EP2018/076423, filed on Sep. 28, 2018.

(30) Foreign Application Priority Data

Sep. 28, 2017 (EP) ..................................... 17193669

(51) Int. Cl.
*B65D 51/24* (2006.01)
*A61K 9/19* (2006.01)
*F26B 5/06* (2006.01)

(52) U.S. Cl.
CPC .............. *B65D 51/241* (2013.01); *A61K 9/19* (2013.01); *F26B 5/06* (2013.01)

(58) Field of Classification Search
CPC ............ F26B 5/06; A61K 9/19; B65D 51/241
(Continued)

(56) References Cited

U.S. PATENT DOCUMENTS 3,454,178 A * 7/1969 Bender ................ B65D 51/241
215/277
4,743,243 A * 5/1988 Vaillancourt ......... A61J 1/2096
604/405
(Continued)

FOREIGN PATENT DOCUMENTS

CN 101082464 A 12/2007
CN 103770967 A 5/2014
(Continued)

OTHER PUBLICATIONS

International Search Report and Written Opinion of the International Searching Authority, PCT/EP2018/076423, dated Nov. 29, 2018, 14 pages.
(Continued)

*Primary Examiner* — Stephen M Gravini
(74) *Attorney, Agent, or Firm* — Bose McKinney & Evans LLP

(57) ABSTRACT

A vial stopper for closure of a lyophilization vial is disclosed. The vial stopper has a stopper body comprising a first circumferential sealing surface for hermetically sealing against an interior surface of a mouth of the vial in a first position of the vial stopper. The stopper body further comprises a second circumferential sealing surface for hermetically sealing against the interior surface of the mouth of the vial in a second position of the vial stopper. The second sealing surface is spaced apart from the first sealing surface in an axial direction of the stopper body. The stopper body further comprises an intermediate region in between the first and second sealing surfaces, the intermediate region having at least one venting element for venting an interior of the vial in at least one intermediate position of the stopper in between the first and second positions.

14 Claims, 7 Drawing Sheets

(58) Field of Classification Search
USPC .................................... 34/92, 284; 215/249
See application file for complete search history.

(56) References Cited

U.S. PATENT DOCUMENTS

| | | | |
|---|---|---|---|
| 4,883,641 A | 11/1989 | Wicks et al. | |
| 5,522,155 A | 6/1996 | Jones | |
| 5,689,895 A * | 11/1997 | Sutherland | F26B 5/06 215/310 |
| 5,894,949 A * | 4/1999 | Taskis | B65D 51/002 215/261 |
| 5,958,778 A * | 9/1999 | Kidd | B01L 3/5021 436/178 |
| 6,199,297 B1 * | 3/2001 | Wisniewski | F26B 5/06 206/439 |
| 6,997,917 B2 * | 2/2006 | Niedospial, Jr. | B65D 47/2031 604/905 |
| 7,520,670 B2 * | 4/2009 | Schwegman | G01K 1/024 374/150 |
| 7,621,412 B2 * | 11/2009 | Raniwala | B65D 51/1616 215/261 |
| 8,171,652 B2 * | 5/2012 | Py | F26B 5/06 34/287 |
| 8,272,411 B2 * | 9/2012 | Py | A61J 1/18 141/351 |
| 9,222,728 B2 * | 12/2015 | Py | F26B 5/06 |
| 10,006,567 B2 * | 6/2018 | Zumbrum | B65D 51/24 |
| 11,319,201 B2 * | 5/2022 | Zumbrum | A61M 39/105 |
| 2004/0011826 A1 | 1/2004 | Stradella | |
| 2008/0039773 A1 * | 2/2008 | Py | F26B 5/06 604/30 |
| 2011/0068106 A1 * | 3/2011 | Zukor | F26B 5/06 220/367.1 |
| 2013/0205719 A1 | 8/2013 | Wensley et al. | |
| 2020/0223604 A1 * | 7/2020 | Heinlein | A61K 9/19 |

FOREIGN PATENT DOCUMENTS

| | | | |
|---|---|---|---|
| DE | 3852061 T2 | 3/1995 | |
| DE | 694 12 291 T2 | 12/1998 | |
| EP | 0 204 486 A2 | 12/1986 | |
| EP | 1680332 A1 * | 7/2006 | .......... B01L 3/50825 |
| FR | 2 767 514 A1 | 2/1999 | |
| GB | 707904 A | 4/1954 | |
| GB | 2 080 776 A | 2/1982 | |
| JP | H07-75672 A | 3/1995 | |
| JP | 2001-206397 A | 7/2001 | |
| JP | 2002-014049 A | 1/2002 | |
| JP | 2012046250 A * | 3/2012 | .......... B01L 3/50825 |
| JP | 2013-245834 A | 12/2013 | |
| WO | WO 93/20869 A1 | 10/1993 | |
| WO | WO 96/06018 A1 | 2/1996 | |
| WO | WO 98/02129 A1 | 1/1998 | |
| WO | WO 00/44641 A2 | 8/2000 | |
| WO | WO-2005042368 A1 * | 5/2005 | .......... B01L 3/50825 |
| WO | WO 2007/035746 A2 | 3/2007 | |
| WO | WO 2008/129409 A1 | 10/2008 | |
| WO | WO 2009/096803 A1 | 8/2009 | |
| WO | WO 2012/168268 A1 | 12/2012 | |
| WO | WO 2013/053620 A1 | 4/2013 | |
| WO | WO-2019063772 A1 * | 4/2019 | ............... A61K 9/19 |

OTHER PUBLICATIONS

Mungikar et al., Effect of the Design of the Stopper Including Dimension, Type, and Vent Area on Lyophilization Process, PDA Journal of Pharmaceutical Science and Technology, 2010, pp. 507-516, vol. 64, No. 6.

Bhambhani, et al., Selection of Containers/Closures for Use in Lyophilization Applications: Possibilities and Limitations, American Pharmaceutical Review, 2010, pp. 86-91, vol. 13, Issue 4.

* cited by examiner

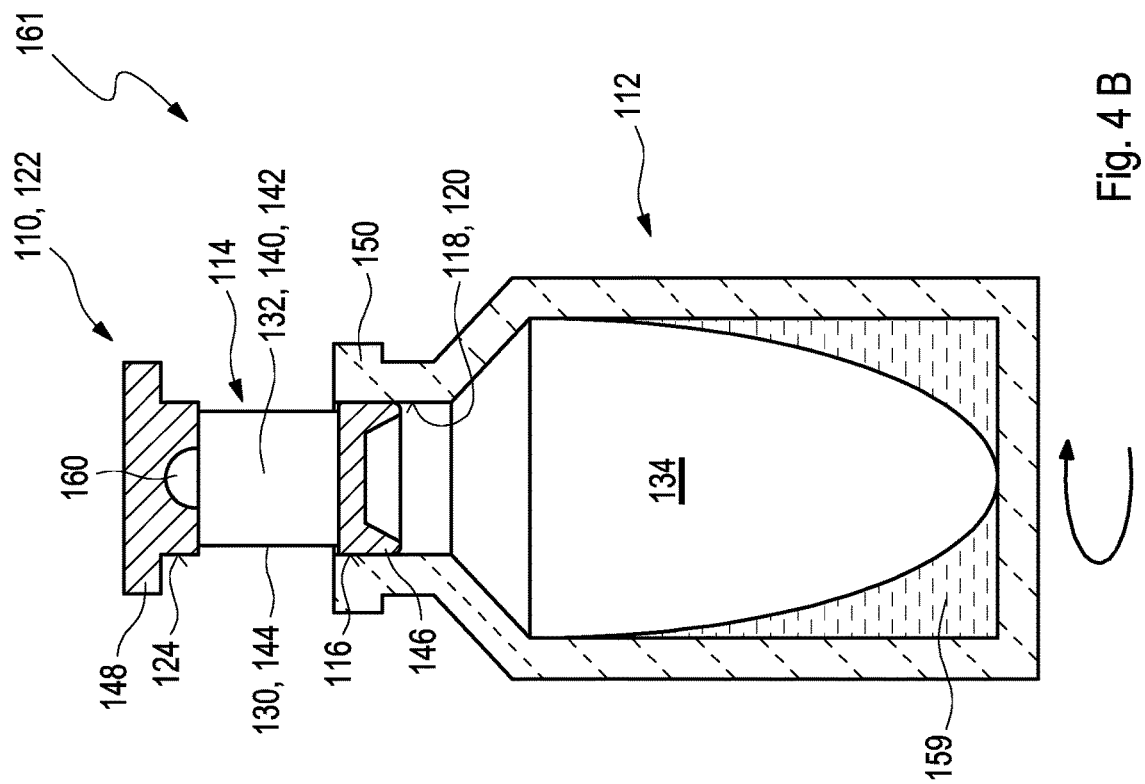
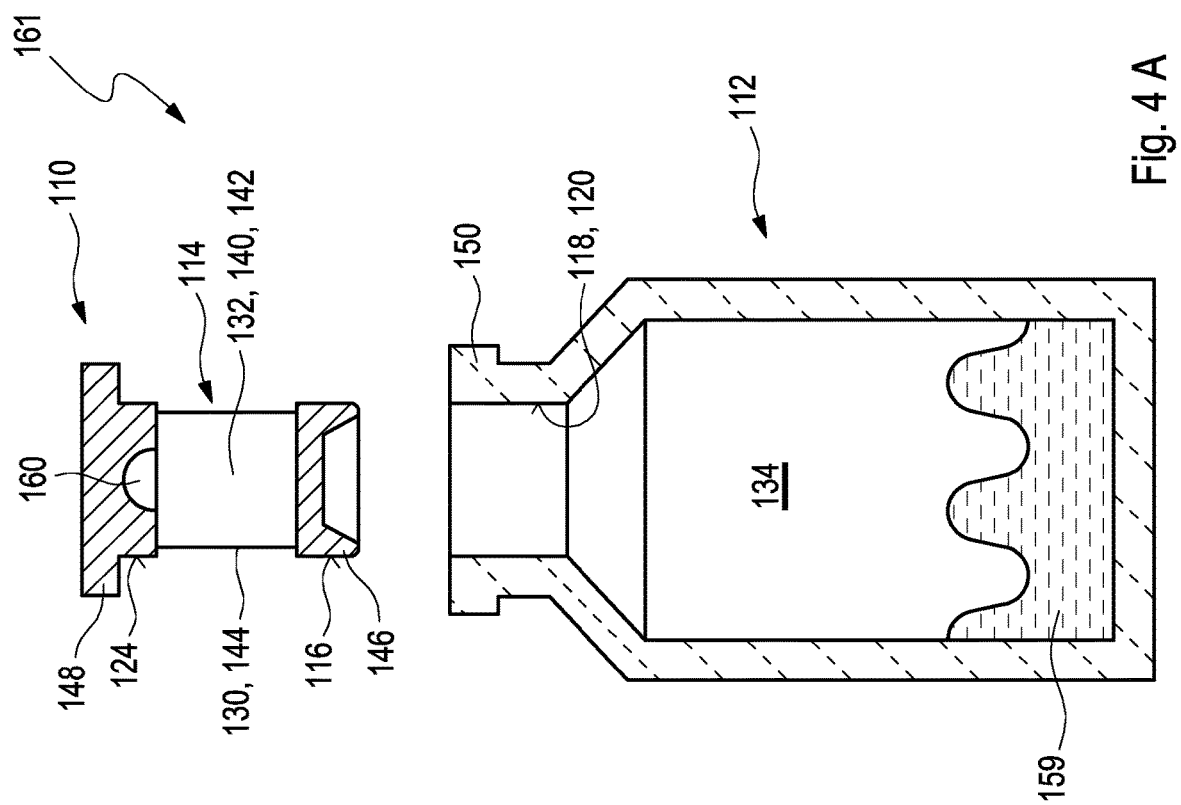

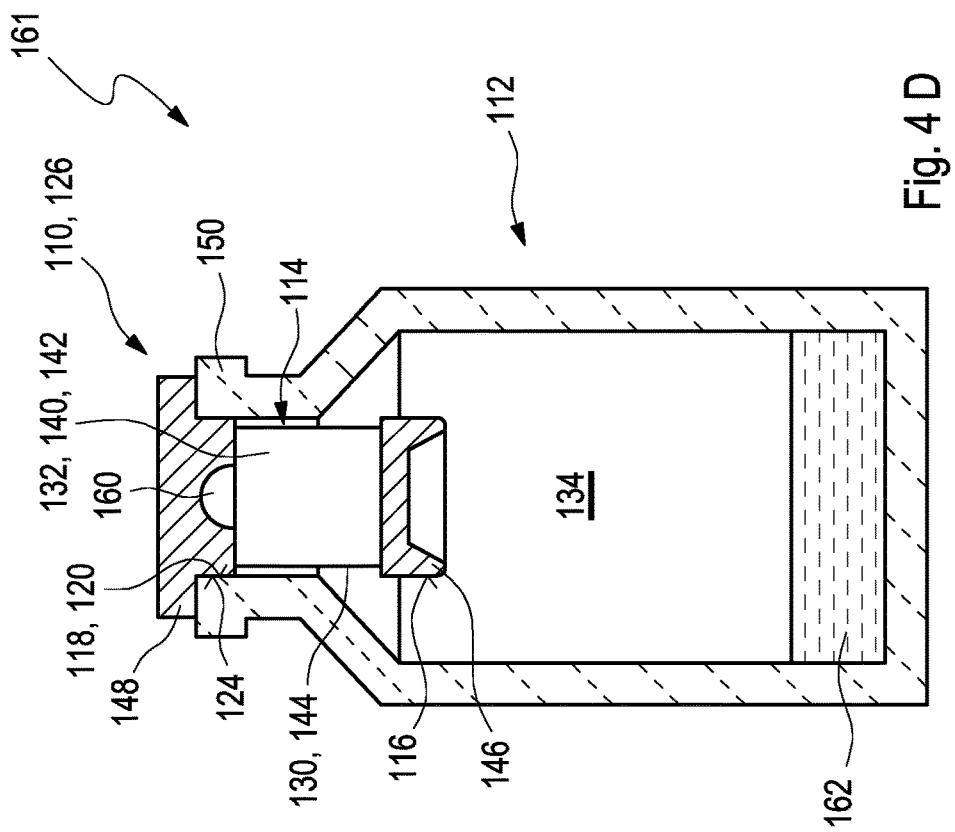
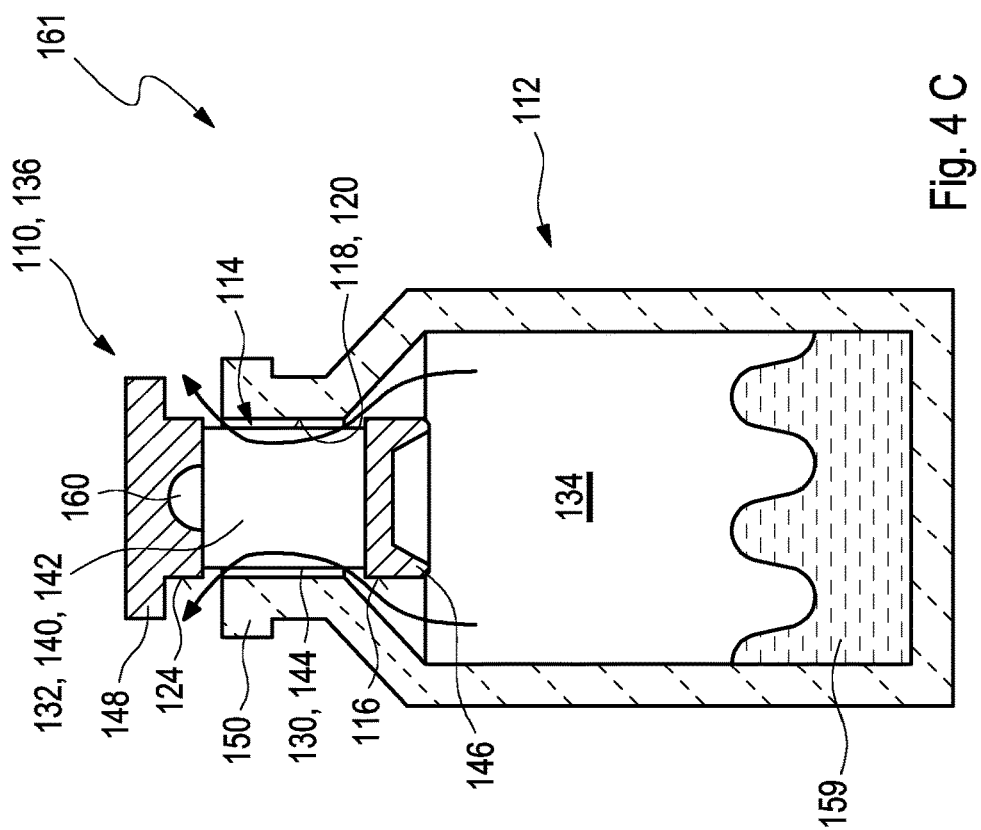

VIAL STOPPER FOR A LYOPHILIZATION VIAL AND CLOSURE METHOD FOR CLOSING A LYOPHILIZATION VIAL

RELATED APPLICATIONS

This application is a continuation of PCT/EP2018/076423, filed Sep. 28, 2018, which claims priority to EP 17 193 669.3, filed Sep. 28, 2017, the entire disclosures of each of which are incorporated herein by reference.

BACKGROUND

This disclosure relates to a vial stopper for the closure of a lyophilization vial and a closure method for closing a lyophilization vial. This disclosure further relates to a lyophilization vial kit, a lyophilization method and a lyophilization apparatus. The devices and methods of this disclosure, as an example, may be used for the preservation of medical or pharmaceutical products in vials, such as drugs or intermediates thereof. Other applications making use of the lyophilization process, for example to preserve foods or biological products, however, are also feasible.

Lyophilization is a dehydration process that usually includes a freezing step that is normally followed by a step of pressure reduction, which allows frozen water in the material to sublime from the solid phase directly to the gas phase. Thus, ensuring control of pressure conditions is usually crucial for successful and hazard-free handling of lyophilization procedures. As a general rule, venting devices that are often integrated into the vial stoppers are used to allow a fast and secure switch between an open and a closed state of the vial or container whose contents may be subject to lyophilization. Thus, a wide variety of vial stoppers for the closure of lyophilization vials and closure methods for closing a lyophilization vial have been described and their effect on the lyophilization process or the lyophilized product studied. Mungikar et al. (Amol Mungikar, Miron Ludzinski and Madhav Kamat: "Effect of the Design of the Stopper Including Dimension, Type, and Vent Area on Lyophilization Process," PDA Journal of Pharmaceutical Science and Technology, Volume 64, Number 6, November-December 2010, pages 507-516), for instance, present a study investigating the role of dimension and design of stoppers on the vapor transfer during the lyophilization process. Bhambhani et al. (Akilesh Bhambhani and Babu Medi: "Selection of Containers/Closures for Use in Lyophilization Applications: Possibilities and Limitations," American pharmaceutical review, Volume 13, Issue 4, May-June 2010, pages 86-91) describe a variety of container closure systems for the lyophilization process as well as their impact on the lyophilization process and on characteristics of the lyophilized product.

A wide range of vial stoppers for the closure of lyophilization vials and closure methods for closing a lyophilization vial have also been described in the patent literature. Thus, WO 1996/006018 A1 describes a lyophilization process and a cap intended for vials or use therewith for containers that are subjected to lyophilization conditions. The cap, which may be resiliently helped in place or screwed on, includes a plug member movable within a fluid passageway in the cap. The plug member while positioned in the fluid passageway is movable between a first upwardly extending venting position and second downwardly engaging, sealing position whereby fluid from the vial or container is precluded from flowing through the fluid passageway in the cap.

WO 1998/002129 A1 describes a device for sealing or connecting a container, having at least one opening with an opening axis, comprising (a) a closure member for arrangement in, at or around the opening and having at least one pierceable part, (b) a connector attachable, when oriented at least partially coaxial with the opening, at a proximal end to the container and at a distal end directly or indirectly to a vessel in the form of a second container, a syringe or a duct, and (c) a sharp operable to penetrate at least the pierceable part and to establish a fluid communication between the container and the vessel. The device comprises that the sharp is connected to or integral with the connector so as to follow it in at least its axial movements, that the connector is axially movable in relation to the closure between at least two defined positions, said positions comprising (i) a first position in which the sharp is axially remote from the closure so as not to pierce it and in which the connector bears on the closure so that an axial force applied to the connector is transmitted to an axial force on the closure and (ii) a second position in which the sharp penetrates the closure, and a releasable locking mechanism arranged to prevent, when engaged, and to permit, when disengaged, movement of the connector from the first to the second position.

Furthermore, WO 2007/035746 A2 describes embodiments of a specimen enclosure apparatus. The specimen enclosure apparatus includes a container having a cavity configured to receive the specimen and an opening extending through a neck of the container to the cavity. An internal flange is positioned intermediate the neck of the container. The specimen enclosure apparatus further includes a closure device configured to be received in the opening. The closure device has a flange seal portion configured to contact the internal flange to form a flange seal proximate the cavity and further has a radial travel limiter integrally formed with the closure device that is configured to contact the container in the opening to limit radial movement of the flange seal portion relative to the internal flange.

Moreover, WO 2013/053620 A1 describes a lid for a sample tube and a sample tube enabling ventilation or sealing depending on the closing position of the lid. Furthermore, a method for drying a sample and a use of the above lid or of the above sample tube for storing or drying a sample are disclosed.

WO 2008/129409 A1 relates to a lyophilization cap for sealing a vial having a mouth ring, said cap comprising: a neck portion having sealing means for sealing said vial; and a head portion having at least one elastically deformable element for engaging behind said mouth ring of said vial.

Further, WO 2000/044641 A2 discloses bulk lyophilization containers including aseptic closure portions or heat flux equalization portions that promote improved bulk lyophilization. Also disclosed are methods of using the bulk lyophilization containers and improved lyophilization stoppers.

Furthermore, DE 69412291 T2 discloses a vial cap intended for use in lyophilization of the vial's contents. The vial cap comprises a cap or stopper body shaped to form a vapor-tight seal with the mouth of the vial or bottle. The vial cap further comprises a venting port that comprises a hole or passage in the cap or stopper body and means for permitting the venting port to be opened or closed off that is activated to be closed by pressing down the cap or stopper body into the mouth of the vial or bottle. The vial cap furthermore comprises a water vapor permeable, sterile barrier venting media that is placed in the path of the vapor travel through the venting port.

FR 2 767 514 A1 describes a container which has two compartments, one formed as a flask and the other as a seal which is shaped to connect with and be able to be displaced into the flask. In this way the two compartments come into contact with each other. This is activated under the action of a stopper that can be perforated and is displaced in the neck of the flask against the force of an elastic retainer.

WO 2009/096803 A1 describes a device which can be used for storing medicinal agents. The inventive bottle comprises a movable tube with longitudinal holes, which tube is arranged in the elongated bottleneck with a fixing ring in such a way that the tube is axially displaceable between the annular recesses made on the outer surface of the tube and a toothed strap for holding a cap in a determined position, wherein the annular recesses with a serrated surface are made on the bottle and the cap. This disclosure makes it possible to reliably store a soluble substance and a solvent and to produce a solution without breaking the insulation between the content and environment.

WO 2007/035746 A2 describes a specimen enclosure apparatus. The specimen enclosure apparatus includes a container having a cavity configured to receive the specimen and an opening extending through a neck of the container to the cavity. An internal flange is positioned intermediate the neck of the container. The specimen enclosure apparatus further includes a closure device configured to be received in the opening. The closure device has a flange seal portion configured to contact the internal flange to form a flange seal proximate the cavity and further has a radial travel limiter integrally formed with the closure device that is configured to contact the container in the opening to limit radial movement of the flange seal portion relative to the internal flange. Containers and closure devices are also provided.

Processes other than lyophilization may also require a switching between an open and a closed state of a container. Thus, GB 707904 A describes fuel supply apparatus for an internal combustion engine, wherein an engine-driven pump delivers the fuel under pressure through a conduit to an opening of fixed size which is alternately opened and closed for periods of time inversely proportional to the engine speed. The fuel supply apparatus is characterized by the feature that an escape valve, inserted in said conduit and urged toward closing position against the pressure of the fuel in said conduit, is adapted to open in response to pressure increase in the conduit and to permit the escape of continuously variable amounts of fuel from the conduit that increase in response to pressure increases in the conduit. The dimensions of the pump and the construction of the escape valve are so correlated with the size of said fixed opening as to permit the pressure of the fuel supplied to the fixed opening to decrease steadily with decreasing pump speed to a degree such as to compensate to a desired extent for the increase in fuel supply to the engine cylinder which would normally result from the increased periods of opening of said fixed opening upon the drop in engine speed occurring when the load on the engine is increased while the engine is running with fully open throttle.

Despite the many advantages of container closure systems developed for the lyophilization process, numerous challenges remain to be tackled. Thus, as an example, the stoppers for the closure of a lyophilization vials and the closure methods for closing a lyophilization vial typically need to meet various requirements contingent to the lyophilization process while the container or the lyophilized content of the container may, as a general rule, have to satisfy further demands relating, for instance, to quality control, product safety or ease of use. There is, consequently, a great need for container closure systems that better consolidate in their layout the qualities that fulfill the diverse requirements at the different steps of production, distribution and use of lyophilized contents than do the devices and methods known in the art.

SUMMARY

This disclosure provides a vial stopper for the closure of lyophilization vials and a closure method for closing a lyophilization vial which at least partially avoid the drawbacks and disadvantages of known methods and devices for the closure of lyophilization vials. Specifically, a vial stopper is disclosed for the closure of a lyophilization vial and a closure method is disclosed for closing a lyophilization vial that better consolidate in their layout the qualities that fulfill the diverse requirements at the different steps of production, distribution and use of lyophilized contents than do the devices and methods known in the art.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "sealing surface," "venting element" and "intermediate position," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. This disclosure may, as the skilled person will recognize, be performed by using alternative features. Similarly, features introduced by "in an embodiment of this disclosure" or similar expressions are intended to be optional features, without any restriction regarding alternative embodiments of this disclosure, without any restrictions regarding the scope of this disclosure and without any restriction regarding the possibility of combining the features introduced in such way with other optional or non-optional features of this disclosure.

In a first aspect of this disclosure, a vial stopper for closure of a lyophilization vial is disclosed. The vial stopper has a stopper body having a first circumferential sealing surface for hermetically sealing against an interior surface of a mouth of the vial in a first position of the vial stopper. The stopper body also has a second circumferential sealing surface for hermetically sealing against the interior surface of the mouth of the vial in a second position of the vial stopper, the second sealing surface being spaced apart from the first sealing surface in an axial direction of the stopper body. The stopper body further comprises an intermediate region in between the first and second sealing surfaces, the intermediate region having at least one venting element for venting an interior of the vial in at least one intermediate position of the stopper in between the first and second positions.

The term "stopper" as used herein is a broad term and is to be given its ordinary and customary meaning to a person of ordinary skill in the art and is not to be limited to a special or customized meaning. The term specifically may refer, without limitation, to an arbitrary closing device configured to at least partly close up a content of a container or an interior of the container against its surroundings when the stopper is inserted into a designated opening of the container. In the following, the terms "stopper" and "vial stopper" may be used interchangeably.

The term "stopper body" as used herein is a broad term and is to be given its ordinary and customary meaning to a person of ordinary skill in the art and is not to be limited to a special or customized meaning. The term specifically may refer, without limitation, to a main part of the stopper that may, for example, provide stability to the stopper as a whole. The stopper body may further fully or partially comprise the main functional parts of the stopper, such as, for example, the first circumferential sealing surface, the second circumferential sealing surface, the intermediate region and the venting elements.

The term "lyophilization" as used herein is a broad term and is to be given its ordinary and customary meaning to a person of ordinary skill in the art and is not to be limited to a special or customized meaning. The term specifically may refer, without limitation, to a process of dehydrating a material by freezing it and subsequently reducing a surrounding pressure to allow frozen water and/or another solvent in the material to sublime directly from the solid phase to the gas phase. The process of lyophilization may also be referred to as freeze-drying, as is known by those of ordinary skill.

The term "lyophilization vial" as used herein is a broad term and is to be given its ordinary and customary meaning to a person of ordinary skill in the art and is not to be limited to a special or customized meaning. The term specifically may refer, without limitation, to a container or flask configured to hold a content in the liquid aggregate condition, in the lyophilized form and during the process of lyophilization. In the following, the lyophilization vial may also be referred to as the vial.

The term "hermetically sealed" as used herein is a broad term and is to be given its ordinary and customary meaning to a person of ordinary skill in the art and is not to be limited to a special or customized meaning. The term specifically may refer, without limitation, to a state in which an opening of a container is closed so tightly that the container cannot leak its content, be it liquid, solid or gaseous, to its surroundings through the opening. Further, fluid, solid or gaseous elements surrounding the container cannot intrude into the container through the opening.

The term "mouth of the vial" as used herein is a broad term and is to be given its ordinary and customary meaning to a person of ordinary skill in the art and is not to be limited to a special or customized meaning. The term specifically may refer, without limitation, to an arbitrary opening of the vial that allows the exchange of a content or an ingredient of the content or the interior of the vial with its surroundings. The opening may further comprise one or several boundaries configured to define, delimit or shape the opening, such as a rim of the vial, a neck of the vial or a portion or element of the neck of the vial. Thus, the opening may, in particular, extend through the neck of the vial or comprise the neck of the vial. Specifically, an interior surface of the mouth of the vial, as described in more detail below, may be part of the neck of the vial.

The term "interior surface of the mouth of the vial" as used herein is a broad term and is to be given its ordinary and customary meaning to a person of ordinary skill in the art and is not to be limited to a special or customized meaning. The term specifically may refer, without limitation, to an arbitrary surface that faces the interior of the vial and at least partially surrounds the mouth of the vial. Thus, the interior surface of the mouth of the vial may be or may be part of the above-mentioned boundaries configured to define, delimit or shape the mouth of the vial. In particular, the interior surface of the mouth of the vial may be part of the neck of the vial.

The term "position" as used herein is a broad term and is to be given its ordinary and customary meaning to a person of ordinary skill in the art and is not to be limited to a special or customized meaning. The term specifically may refer, without limitation, to a designated place or location into which a first object may be brought. Said place or location may, in particular, distinguish itself or be characterized by the physical and/or functional relation of the first object to a second object.

The term "venting element" (also referred to herein as a "vent") as used herein is a broad term and is to be given its ordinary and customary meaning to a person of ordinary skill in the art and is not to be limited to a special or customized meaning. The term specifically may refer, without limitation, to an arbitrary element, arrangement, setup or configuration of another element or device that allows an exchange or interchange of the content of the container or of the interior of the container or of parts of the content of the container or of parts of the interior of the container with its surroundings. In particular, the at least one venting element may be configured to bring about a connection, specifically a fluid connection, between the interior of the vial and the exterior of the vial. Specifically, the venting element may allow the exchange of a gaseous amount of the content or an ingredient of the content of the container with the surroundings of the container. Thus, the venting element may, in particular, facilitate an equalization of pressure between the interior of the container and its surroundings. The venting element may comprise at least one venting slot. As used herein, the term "venting slot" may generally refer to a venting element or vent whose dimension in a first direction in space exceeds its dimension in at least one second direction in space at least by a factor of 2, preferably by a factor of 5, more preferably by a factor of 10. The venting slot may, in particular, extend in an axial direction of the stopper body. The venting element may further comprise at least one venting opening extending through the stopper body. Specifically, the venting opening may extend through the stopper body in a non-axial direction of the stopper body. In particular, the venting opening may extend through the stopper body in a direction selected from the group consisting of: a radial direction intersecting with an axis of the stopper body; a secantial direction perpendicular to an axis of the stopper body without intersecting with the axis. Specifically, the venting opening may form at least one through hole through the stopper body, wherein the through hole is elongated in an axial direction of the stopper body. Other geometric forms and arrangements of venting elements than those explicitly described here are also feasible.

The venting element, in particular the venting slot, may have a length. The term "length of the venting element" as used herein is a broad term and is to be given its ordinary and customary meaning to a person of ordinary skill in the art and is not to be limited to a special or customized meaning. The term specifically may refer, without limitation, to a dimension of the venting element extending in the axial direction of the stopper body.

Further, the interior surface of the mouth of the vial may have a height. The term "height of the interior surface of the mouth of the vial" as used herein is a broad term and is to be given its ordinary and customary meaning to a person of ordinary skill in the art and is not to be limited to a special or customized meaning. The term, specifically, may refer, without limitation, to a dimension of the interior surface of the mouth of the vial extending in an axial direction of the vial. Thus, the interior surface of the mouth of the vial may typically have the shape of a cylinder jacket. In such a case the height of the interior surface of the vial may be the height of the cylinder jacket.

The length of the venting element, in particular the venting slot, may exceed the height of the interior surface of the mouth of the vial. Thus, when the vial stopper is placed in the intermediate position, the venting element, in particular the venting slot, may protrude beyond the interior surface of the mouth of the vial into both the interior of the vial and the outside of the vial thereby establishing a fluid connection between the interior of the vial and the outside of the vial in order to allow the exchange of a gaseous amount of the content or an ingredient of the content or the interior of the vial with the surroundings of the vial. In particular, the length of the venting element, specifically the venting slot, may exceed the height of the interior surface of the mouth of the vial by 2 mm to 10 mm, preferably by 4 mm, such that the venting element, in particular the venting slot, may protrude, for example 1 mm to 5 mm, preferably 2 mm, into both the interior of the vial and the outside of the vial.

Further, the vial stopper, in particular the stopper body, may comprise a central cavity that is formed separate from the at least one venting element and that may be arranged within the stopper body. In particular, the central cavity may facilitate the withdrawal of an amount of the content of the vial by the retrieval device, in particular when the vial is in an upright position. Specifically, the central cavity may be open towards the interior of the vial. Thus, the central cavity may allow the retrieval device to be inserted into the interior of the vial by piercing merely the stopper head of the vial stopper.

The vial stopper may have 2 to 10 venting elements, specifically 4 to 8 venting elements, more specifically 6 venting elements. Further, an overall cross-sectional area of the vial stopper in the intermediate region through the at least one venting element and perpendicular to an axis of the stopper body may be 60% to 90% of a cross-sectional area of the mouth of the vial, specifically 70% to 80% and more specifically 75%. The cross-sectional area of the mouth of the vial is to be taken such that it comprises the overall cross-sectional area of the vial stopper in the intermediate region through the at least one venting element and perpendicular to an axis of the stopper body. Thus, the cross-sectional area of the mouth of the vial is perpendicular to the axis of the stopper body when the stopper body is inserted into the mouth of the vial. In particular, the intermediate region may have an essentially cylindrical shape, specifically a circular cylindrical shape. Furthermore, both the first and the second sealing surface may have cylindrical shapes, specifically circular cylindrical shapes, wherein the first and second sealing surfaces may have identical diameters.

In an alternative embodiment, the overall cross-sectional area of the vial stopper in the intermediate region through the at least one venting element and perpendicular to an axis of the stopper body may exceed 90% of the cross-sectional area of the mouth of the vial. In particular, this may apply to embodiments of the vial stopper, wherein the vial stopper does not comprise the central cavity as described above. Specifically, an overall cross-sectional area of the vial stopper in the intermediate region through the at least one venting element and perpendicular to an axis of the stopper body may cover a range from 90% to 98%, specifically 95% to 98% of the cross-sectional area of the mouth of the vial. Accordingly, the at least one venting element, in particular the venting slot, may provide for a range from 2% to 10%, specifically 2% to 5% of the cross-sectional area of the mouth of the vial to be kept open when the stopper is inserted into the mouth of the vial in the intermediate position to allow the venting of the interior of the vial.

The venting element, in particular the venting slot, may be formed as to allow a gas exchange between the interior and the exterior of the vial without compromising either the mechanical stability of the stopper or the ability of the first and second circumferential sealing surfaces and the intermediate region exempt from the venting element to fit flush with the interior surface of the mouth of the vial. In particular, the venting element, specifically the venting slot, may have a depth in a radial direction intersecting with an axis of the stopper body in the range of 1 mm to 5 mm, specifically 2 mm to 3 mm.

The term "sealing surface" as used herein is a broad term and is to be given its ordinary and customary meaning to a person of ordinary skill in the art and is not to be limited to a special or customized meaning. The term specifically may refer, without limitation, to an arbitrary surface configured to interact with a second surface or object in such a way as to prevent the passage of a liquid and/or a gas and/or a solid, such as, for example a powder, between the sealing surface and the second surface or object. The sealing surface may, in particular, be or may comprise a circumferential sealing surface. Thus, the term "sealing surface" may in particular refer to a circumferential sealing surface. The term "circumferential sealing surface" as used herein is a broad term and is to be given its ordinary and customary meaning to a person of ordinary skill in the art and is not to be limited to a special or customized meaning. The term specifically may refer, without limitation, to a sealing surface that at least partially surrounds at least one object. In particular, the circumferential sealing surface may comprise a periphery or perimeter of the object. Specifically, the object may be of circular or elliptic or cylindrical shape, such as for example the neck of the vial. Thus, the circumferential sealing surface may particularly have the shape of a cylinder jacket. In particular, the "first circumferential sealing surface" may also be referred to as the "first sealing surface" and the "second circumferential sealing" surface may be referred to as the "second sealing surface." In particular, the first and second sealing surfaces may have a larger diameter than the intermediate region. Further, the stopper body may be essentially rotationally symmetrical about an axis. Furthermore, the first and second circumferential sealing surfaces may both be shaped as surfaces of a circular cylinder ring about an axis of the stopper body. The first and second circumferential sealing surfaces may, in particular, both have identical diameters.

An end of the stopper facing the vial may be shaped as a closed flat circular surface. The vial stopper may further comprise at least one stopper head at an outer end of the stopper body, for placing onto an outer rim of the mouth of the vial, the stopper head having a larger diameter than the stopper body. In particular, the stopper body and the stopper head may be integrally formed. Further, the stopper body may be integrally formed. Specifically, the stopper body may be fully or partially made of a plastic material. The stopper body may, in particular, be fully or partially made of at least one material selected from the group consisting of butyl rubber, bromobutyl rubber and chlorobutyl rubber. Further, the stopper body, in the intermediate region, may have a plurality of protrusions on an outer surface, specifically, a plurality of spherical protrusions or partially spherical protrusions.

In a second aspect of this disclosure, a lyophilization vial kit is disclosed. The lyophilization vial kit comprises at least one lyophilization vial and at least one vial stopper according to this disclosure. The lyophilization vial has a mouth dimensioned to interact with the vial stopper such that, in a first position of the vial stopper in the mouth, the first circumferential sealing surface hermetically seals against an interior surface of a mouth, wherein, in a second position of the vial stopper in the mouth, the second circumferential sealing surface hermetically seals against an interior surface of a mouth, wherein, in the intermediate position in between the first and second positions, the interior of the vial is vented via the at least one venting element. Specifically, the first position, the intermediate position and the second position may be positions of the vial stopper relative to the vial, wherein the first position, the intermediate position and the second position may be sequentially reached, in the given order, when the vial stopper is pushed into the mouth of the vial. Accordingly, the second position, the intermediate position and the first position may be sequentially reached, in the given order, when the vial stopper is retracted from the mouth of the vial starting in the second position. The lyophilization vial kit may further comprise a flange cap, the flange cap being configured for being placed on top of the vial stopper and flanging the vial stopper against an outer rim of the vial.

Furthermore, the stopper may be configured such that a liquid contained in the lyophilization vial is completely removable from the vial with the stopper in the second position by inserting a retrieval device through the vial stopper or the stopper head into the venting element when the vial is in an upside-down position. Such a configuration of the stopper may be reached by a suitable arrangement, in particular a spatial arrangement, and/or a design of the at least one venting element as described above and as will be described in more detail further below by reference to an embodiment of this disclosure as illustrated in FIGS. 2A to 2D. As used herein, the term "retrieval device" may generally refer to a device configured to remove a liquid contained in the vial through the vial stopper. In particular, the retrieval device may be at least partially insertable into the vial by piercing the vial stopper and/or the stopper head. The retrieval device may specifically be selected from the group consisting of: a cannula; a tube; a drain tube; a mandrel; a syringe.

In an alternative embodiment, the liquid contained in the lyophilization vial may not be completely removable from the vial with the stopper in the second position by inserting a retrieval device through the vial stopper or the stopper head into the venting element when the vial is in an upside-down position. In such an embodiment, as will be described in more detail further below and illustrated by FIGS. 1A to 1D, the stopper body may comprise a central cavity which is in fluidic connection to the interior volume of the vial. In particular, the retrieval device may be inserted into the vial by piercing the stopper and/or the stopper head and introducing the retrieval device into the central cavity.

In a third aspect of this disclosure, a closure method for closing a lyophilization vial is disclosed. The method comprises the following steps, preferably in the designated order. An order other than the designated order may generally be possible. Further, one or several or all of the steps may be carried out repeatedly. Furthermore, two or more steps may be carried out simultaneously or in a fully or partially temporally overlapping fashion. The method may in addition to the steps specified below comprise further steps.

The closure method comprises the following steps:
a) providing at least one lyophilization vial kit according to a lyophilization vial kit of this disclosure;
b) pushing the vial stopper into the mouth of the vial until the first position is reached;
c) pushing the vial stopper further into the mouth of the vial until the intermediate position is reached, whereby the interior of the vial is vented; and
d) pushing the vial stopper further into the mouth of the vial until the second position is reached.

In particular after each of steps b), c) and d), the lyophilization vial kit may remain in the respective position for at least 3 seconds. Further, after method step b) and before method step c), an optical inspection step of the content of the vial to detect the presence of at least one solid component contained in the vial may be performed. Specifically, the component may be a particle, e.g., glass particle, dust particle, metallic particle. Thus, the optical inspection step may, specifically, contribute to or be part of a quality control of the content of the vial. In particular, during the inspection step, the vial may be rotated.

In a fourth aspect of this disclosure, a lyophilization method is disclosed. The method comprises the following steps, preferably in the designated order. An order other than the designated order may generally be possible. Further, one or several or all of the steps may be carried out repeatedly. Furthermore, two or more steps may be carried out simultaneously or in a fully or partially temporally overlapping fashion. The method may in addition to the steps specified below comprise further steps.

The lyophilization method comprises the following steps:
i) providing at least one lyophilization vial kit according to a lyophilization vial kit of this disclosure;
ii) filling at least one liquid into the vial;
iii) pushing the vial stopper into the mouth of the vial until the first position is reached;
iv) pushing the vial stopper further into the mouth of the vial until the intermediate position is reached;
v) performing at least one lyophilization process, with the vial stopper in the intermediate position, thereby transferring the liquid into at least one solid material, with at least one gaseous substance being vented from the interior of the vial through the venting element; and vi) pushing the vial stopper further into the mouth of the vial until the second position is reached.

The method may optionally be fully or partially computer-controlled.

In particular, with the vial stopper in the first position, an optical inspection step may be performed. In particular, the optical inspection step may be an optical inspection step of at least one component contained in the vial. Specifically, the component may be a chemical substance and/or a particle, in particular, a contaminant. Thus, the optical inspection step may, specifically, contribute to or be part of a quality control of the content of the vial. In particular, during the inspection step, the vial may be rotated.

In a fifth aspect of this disclosure, a lyophilization apparatus is disclosed. The lyophilization apparatus comprises:

A) a plurality of lyophilization vial kits according to a lyophilization vial kit of this disclosure;

B) at least one filling device for filling at least one liquid into the vials of the lyophilization vial kits;

C) at least one pushing device for pushing the vial stoppers of the vials into the mouths of the vials in a stepwise fashion, thereby sequentially bringing the vial stoppers into the first position, the intermediate position and the second position;

D) a temperature application device; and

E) a pressure application device.

The term "temperature application device" (also referred to herein as "temperature applicator") as used herein is a broad term and is to be given its ordinary and customary meaning to a person of ordinary skill in the art and is not to be limited to a special or customized meaning. The term specifically may refer, without limitation, to an arbitrary device configured to heat and/or cool an object and/or to control a temperature of the object. In particular, the temperature application device may be configured to adjust the temperature of the object to a predefined value. Thus, the temperature application device may comprise a heating device, for example a heating device having a heating resistor. The temperature application device may further comprise a cooling device. In particular, the temperature application device may be configured to measure the temperature of the object.

The term "pressure application device" (also referred to herein as "pressure applicator") as used herein is a broad term and is to be given its ordinary and customary meaning to a person of ordinary skill in the art and is not to be limited to a special or customized meaning. The term specifically may refer, without limitation, to an arbitrary device configured to increase and/or decrease a pressure within a room, a chamber or a defined space. The pressure application device may in particular be configured to control the pressure of the room, the chamber or the defined space and/or adjust the pressure of the room, the chamber or the defined space to a predefined value. The pressure application device may specifically be configured to apply a positive pressure and/or a negative pressure, such as a vacuum or a partial vacuum, to the room, the chamber or the defined space. The pressure application device may, specifically, comprise one or several pumps and/or valves. The pressure application device may particularly be configured to measure the pressure of the room, the chamber or the defined space.

The lyophilization apparatus may further comprise:

F) at least one optical inspection device for optically inspecting the lyophilization vial kits.

The lyophilization apparatus may further comprise:

G) at least one controller for controlling a lyophilization sequence, wherein, specifically, the controller may be configured for controlling the lyophilization apparatus to perform the lyophilization method according to a lyophilization method of this disclosure.

Summarizing and without excluding further possible embodiments, the following embodiments may be envisaged:

Embodiment 1

A vial stopper for closure of a lyophilization vial, the vial stopper having a stopper body, the stopper body comprising a first circumferential sealing surface for hermetically sealing against an interior surface of a mouth of the vial in a first position of the vial stopper, the stopper body further comprising a second circumferential sealing surface for hermetically sealing against the interior surface of the mouth of the vial in a second position of the vial stopper, the second sealing surface being spaced apart from the first sealing surface in an axial direction of the stopper body, the stopper body further comprising an intermediate region in between the first and second sealing surfaces, the intermediate region having at least one venting element for venting an interior of the vial in at least one intermediate position of the stopper in between the first and second positions.

Embodiment 2

The vial stopper according to the preceding embodiment, wherein the venting element comprises at least one venting slot.

Embodiment 3

The vial stopper according to the preceding embodiment, wherein the venting slot extends in an axial direction of the stopper body.

Embodiment 4

The vial stopper according to any one of the preceding embodiments, wherein the venting element comprises at least one venting opening extending through the stopper body.

Embodiment 5

The vial stopper according to the preceding embodiment, wherein the venting opening extends through the stopper body in a non-axial direction of the stopper body.

Embodiment 6

The vial stopper according to any one of the two preceding embodiments, wherein the venting opening extends through the stopper body in a direction selected from the group consisting of: a radial direction intersecting with an axis of the stopper body; a secantial direction perpendicular to an axis of the stopper body without intersecting with the axis.

Embodiment 7

The vial stopper according to any one of the three preceding embodiments, wherein the venting opening comprises at least one through hole through the stopper body, wherein the through hole is elongated in an axial direction of the stopper body.

Embodiment 8

The vial stopper according to any one of the preceding embodiments, wherein the vial stopper comprises 2 to 10 venting elements, specifically 4 to 8 venting elements, more specifically 6 venting elements.

Embodiment 9

The vial stopper according to any one of the preceding embodiments, wherein an overall cross-sectional area of the vial stopper in the intermediate section region through the at least one venting element and perpendicular to an axis of the stopper body is 60% to 90% of a cross-sectional area of the mouth of the vial, specifically 70% to 80% and more specifically 75%.

Embodiment 10

The vial stopper according to any one of the preceding embodiments, wherein the at least one venting element provides for a range from 2% to 10%, specifically 2% to 5% of the cross-sectional area of the mouth of the vial to be kept open when the vial stopper is inserted into the mouth of the vial in the intermediate position.

Embodiment 11

The vial stopper according to any one of the preceding embodiments, wherein the intermediate region has an essentially cylindrical shape, specifically a circular cylindrical shape.

Embodiment 12

The vial stopper according to any one of the preceding embodiments, wherein both the first and the second sealing surface have cylindrical shapes, specifically circular cylindrical shapes, wherein the first and second sealing surfaces have identical diameters.

Embodiment 13

The vial stopper according to the preceding embodiment, wherein the first and second sealing surfaces have a larger diameter than the intermediate region.

Embodiment 14

The vial stopper according to any one of the preceding embodiments, wherein the stopper body essentially is rotationally symmetrical about an axis.

Embodiment 15

The vial stopper according to any one of the preceding embodiments, wherein the first and second circumferential sealing surfaces both are shaped as surfaces of a circular cylinder ring about an axis of the stopper body.

Embodiment 16

The vial stopper according to the preceding embodiment, wherein the first and second circumferential sealing surfaces both have identical diameters.

Embodiment 17

The vial stopper according to any one of the preceding embodiments, wherein an end of the stopper facing the vial is shaped as a closed flat circular surface.

Embodiment 18

The vial stopper according to any one of the preceding embodiments, wherein the vial stopper further comprises at least one stopper head at an outer end of the stopper body, for placing onto an outer rim of the mouth of the vial, the stopper head having a larger diameter than the stopper body.

Embodiment 19

The vial stopper according to the preceding embodiment, wherein the stopper body and the stopper head are formed integrally.

Embodiment 20

The vial stopper according to any one of the preceding embodiments, wherein the stopper body is formed integrally.

Embodiment 21

The vial stopper according to the preceding embodiment, wherein the stopper body is fully or partially made of a plastic material.

Embodiment 22

The vial stopper according to the preceding embodiment, wherein the stopper body is fully or partially made of at least one material selected from the group consisting of butyl rubber, bromobutyl rubber and chlorobutyl rubber.

Embodiment 23

The vial stopper according to any one of the preceding embodiment, wherein the stopper body, in the intermediate region, has a plurality of protrusions on an outer surface, specifically a plurality of spherical protrusions or partially spherical protrusions.

Embodiment 24

A lyophilization vial kit, the kit comprising at least one lyophilization vial and at least one vial stopper according to any one of the preceding embodiments, wherein the lyophilization vial has a mouth dimensioned to interact with the vial stopper in such a way that, in a first position of the vial stopper in the mouth, the first circumferential sealing surface hermetically seals against an interior surface of a mouth, wherein, in a second position of the vial stopper in the mouth, the second circumferential sealing surface hermetically seals against an interior surface of a mouth, wherein, in the intermediate position in between the first and second positions, the interior of the vial is vented to the outside of the vial via the at least one venting element.

Embodiment 25

The lyophilization vial kit according to the preceding embodiment, wherein the first position, the intermediate position and the second position are positions of the vial stopper relative to the vial, wherein the first position, the intermediate position and the second position are sequentially reached, in the given order, when the vial stopper is pushed into the mouth of the vial.

Embodiment 26

The lyophilization vial kit according to any of the two preceding embodiments, wherein the second position, the intermediate position and the first position are positions of the vial stopper relative to the vial, wherein the second position, the intermediate position and the first position are sequentially reached, in the given order, when the vial stopper is retracted from the mouth of the vial starting in the second position.

Embodiment 27

The lyophilization vial kit according to any one of the two preceding embodiments, the lyophilization vial kit further comprising a flange cap, the flange cap being configured for being placed on top of the vial stopper and flanging the vial stopper against an outer rim of the vial.

Embodiment 28

The lyophilization vial kit according to any on of the preceding embodiments, wherein the stopper is configured such that a liquid contained in the lyophilization vial is completely removable from the vial with the stopper in the second position by inserting a retrieval device into the venting element when the vial is in an upside-down position.

Embodiment 29

A closure method for closing a lyophilization vial, the method comprising the following steps:
a) providing at least one lyophilization vial kit according to any one of the preceding embodiments referring to a lyophilization vial kit;
b) pushing the vial stopper into the mouth of the vial until the first position is reached;
c) pushing the vial stopper further into the mouth of the vial until the intermediate position is reached, whereby the interior of the vial is vented; and
d) pushing the vial stopper further into the mouth of the vial until the second position is reached.

Embodiment 30

The closure method according to the preceding embodiment, wherein, after each of steps b), c) and d), the lyophilization vial kit remains in the respective position for at least 3 seconds.

Embodiment 31

The closure method according to any one of the preceding embodiments referring to a closure method, wherein, after method step b) and before method step c), an optical inspection step of at least one component contained in the vial is performed.

Embodiment 32

The closure method according to the preceding embodiment, wherein, during the inspection step, the vial is rotated.

Embodiment 33

A lyophilization method, comprising:
i) providing at least one lyophilization vial kit according to any one of the preceding embodiments referring to a lyophilization vial kit;
ii) filling at least one liquid into the vial;
iii) pushing the vial stopper into the mouth of the vial until the first position is reached;
iv) pushing the vial stopper further into the mouth of the vial until the intermediate position is reached;
v) performing at least one lyophilization process, with the vial stopper in the intermediate position, thereby transferring the liquid into at least one solid material, with at least one gaseous substance being vented from the interior of the vial through the venting element; and
vi) pushing the vial stopper further into the mouth of the vial until the second position is reached.

Embodiment 34

The lyophilization method according to the preceding embodiment, wherein, with the vial stopper in the first position, an optical inspection step is performed.

Embodiment 35

The lyophilization method according to the preceding embodiment, wherein, during the optical inspection step, the vial is rotated.

Embodiment 36

A lyophilization apparatus, comprising:
A) a plurality of lyophilization vial kits according to any one of the preceding embodiments referring to a lyophilization vial kit;
B) at least one filling device for filling at least one liquid into the vials of the lyophilization vial kits;
C) at least one pushing device for pushing the vial stoppers of the vials into the mouths of the vials in a stepwise fashion, thereby sequentially bringing the vial stoppers into the first position, the intermediate position and the second position;
D) a temperature application device; and
E) a pressure application device.

Embodiment 37

The lyophilization apparatus according to the preceding embodiment, wherein the temperature application device comprises at least one cooling device for cooling the lyophilization vial kits.

Embodiment 38

The lyophilization apparatus according to any one of the preceding embodiments referring to a lyophilization apparatus, further comprising:
F) at least one optical inspection device for optically inspecting the lyophilization vial kits.

Embodiment 39

The lyophilization apparatus according to any one of the preceding embodiments referring to a lyophilization apparatus, further comprising:

G) at least one controller for controlling a lyophilization sequence, wherein, specifically, the controller is configured for controlling the lyophilization apparatus to perform the lyophilization method according to any one of the preceding embodiments referring to a lyophilization method.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIGS. 4A to 4D show selected steps of a lyophilization method according to this disclosure.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
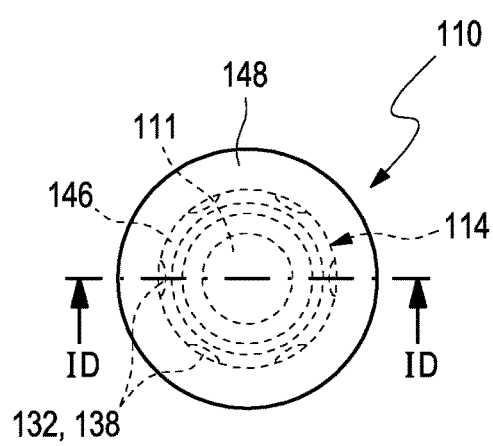
FIGS. 1A, 1B, 1C and 1D show a vial stopper according to this disclosure in top view (1A), in front view (1B), in bottom view (1C) and in a cross-sectional view (1D)
FIG. 1E shows a cross-sectional view of another embodiment of a vial stopper according to this disclosure.
Figure 1:
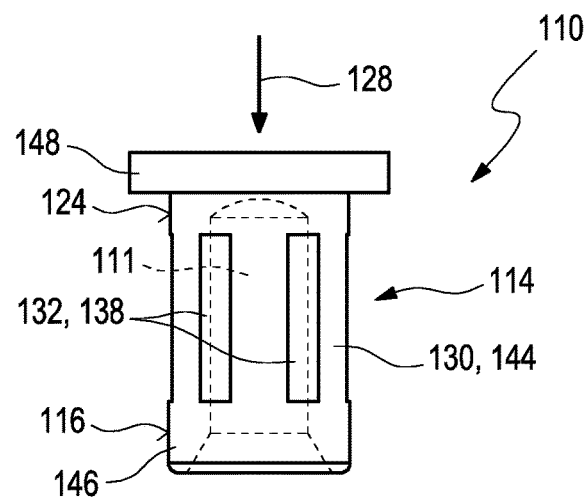
Figure 1:
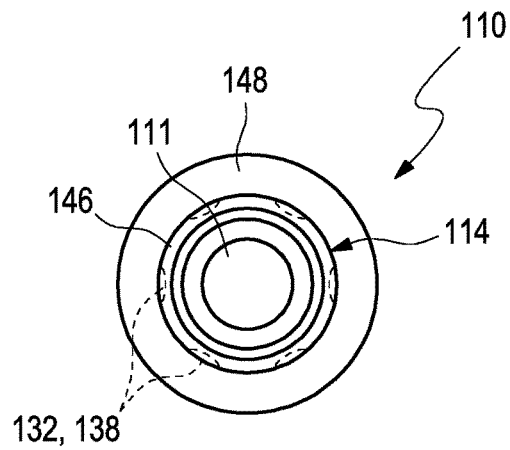
Figure 1:
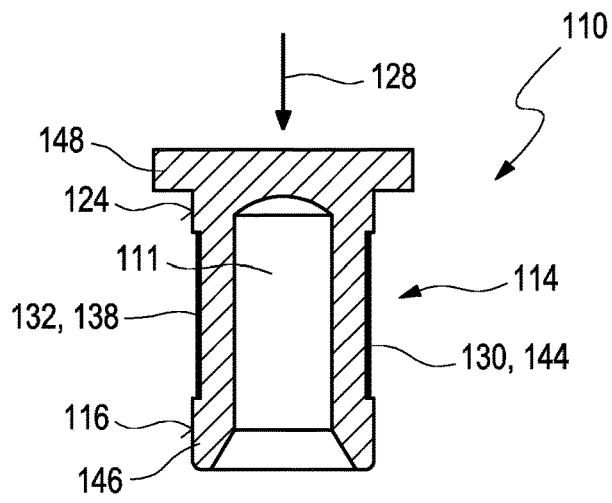
Figure 1:
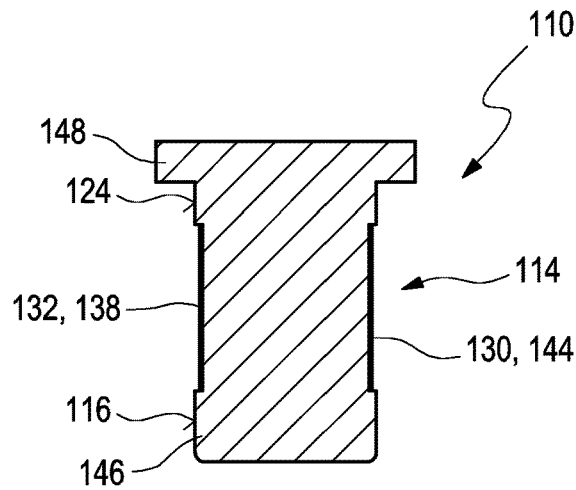
Figure 2:
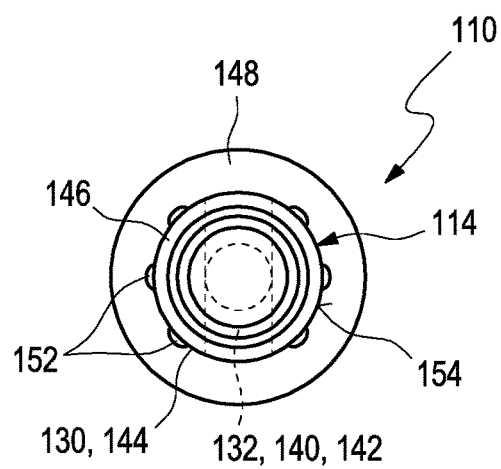
FIGS. 2A, 2B, 2C and 2D show another embodiment of a vial stopper according to this disclosure in bottom view (2A), in front view (2B), in side view (2C) and in a cross-sectional view (2D)
Figure 2:
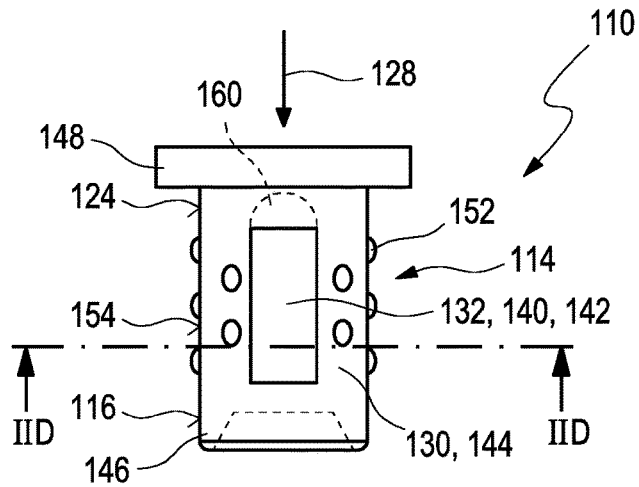
Figure 2:
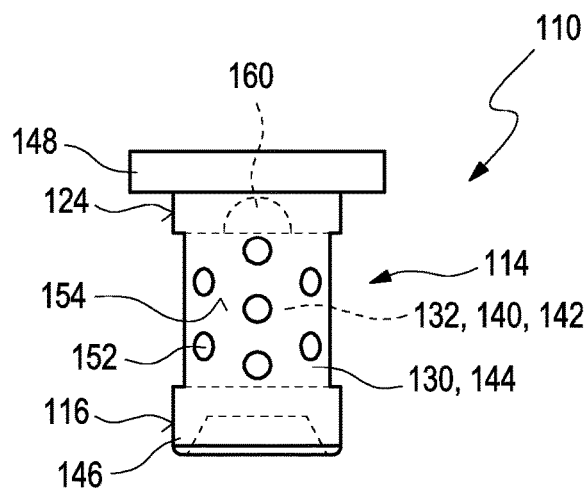
Figure 2:
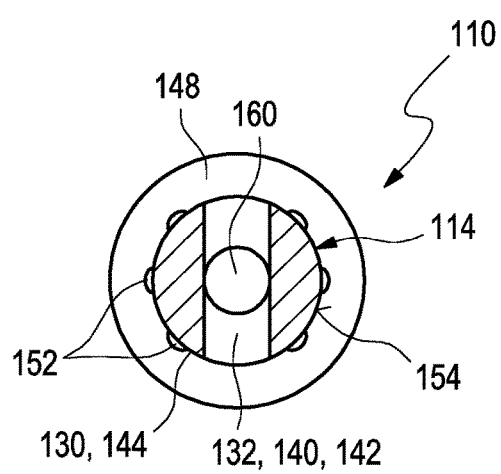

FIGS. 1A to 1D show an embodiment of a vial stopper 110 according to this disclosure in top view (1A), in front view (1B) in bottom view (1C) and in a cross-sectional view (1D). The sectional plane along which the vial stopper is cut to produce the cross-sectional view in FIG. 1D is indicated in FIG. 1A by a line marked with ID. FIG. 1E shows a cross-sectional view of another embodiment of the vial stopper 110 according to this disclosure that does not comprise a cavity 111 and FIGS. 2A to 2D show another embodiment of a vial stopper 110 according to this disclosure in bottom view (2A), in front view (2B) in side view (2C) and in cross-sectional view (2D). The sectional plane along which the vial stopper is cut to produce the cross-sectional view in FIG. 2D is indicated in FIG. 2B by a line marked with HD. The vial stopper 110 for closure of a lyophilization vial 112 has a stopper body 114 comprising a first circumferential sealing surface 116 for hermetically sealing against an interior surface 118 of a mouth 120 of the vial 112 in a first position 122 of the vial stopper 110. The stopper body 114 further comprises a second circumferential sealing surface 124 for hermetically sealing against the interior surface 118 of the mouth 120 of the vial 112 in a second position 126 of the vial stopper 110, the second sealing surface 124 being spaced apart from the first sealing surface 116 in an axial direction 128 of the stopper body 114. The stopper body 114 further comprises an intermediate region 130 in between the first 116 and second sealing surfaces 124, the intermediate region 130 having at least one venting element (or "vent") 132 for venting an interior 134 of the vial 112 in at least one intermediate position 136 of the stopper 110 in between the first 122 and second positions 126.

The venting element 132 may comprise at least one venting slot 138 as shown in FIGS. 1A to 1D. The venting slot 138 may, in particular, extend in an axial direction 128 of the stopper body 114. Additionally or alternatively, the venting element 132 may further comprise at least one venting opening 140 extending through the stopper body 114, as depicted in FIGS. 2A to 2D. Specifically, the venting opening 140 may extend through the stopper body in a non-axial direction of the stopper body 114. In particular, the venting opening 140 may extend through the stopper body 114 in a radial direction intersecting with an axis of the stopper body 114, as shown in FIGS. 2A to 2D. The venting opening 140 may, however, also extend in a secantial direction perpendicular to an axis of the stopper body 114 without intersecting with the axis (not shown in the Figures). Specifically, the venting opening 140 may comprise at least one through hole 142 through the stopper body 114, wherein the through hole 142 is elongated in an axial direction 128 of the stopper body 114. Other geometric forms and arrangements of venting elements 132 than those explicitly described here are also feasible.

The vial stopper 110 may comprise a central cavity 111 as depicted in FIGS. 1A to 1D. The central cavity 111 may be formed separate from the at least one venting element 132, as illustrated in FIGS. 1A to 1D. The central cavity 111 may be arranged within the stopper body 114 and may, in particular, be open towards the interior 134 of the vial 112, as can for example be seen from FIGS. 1B and 1D. In particular, the central cavity 111 may facilitate the withdrawal of an amount of the content of the vial 112 by a retrieval device 143, in particular when the vial is in an upright position. Specifically, the central cavity 111 may be open towards the interior 134 of the vial 112. Thus, the central cavity 111 may allow the retrieval device 143 to be inserted into the interior 134 of the vial 112 by piercing merely a stopper head 148 of the vial stopper 110. In another embodiment of the vial stopper 110 as shown in FIG. 1E, the vial stopper does not comprise a central cavity 111. Such an embodiment of the vial stopper 110 may also be referred to as a full-mold cast version. In the case of the vial stopper 110 comprising a central cavity 111 a smaller amount of material must be traversed and/or pierced to insert the retrieval device 143 through the vial stopper into the lyophilization vial as compared to the full-mold cast version.

The vial stopper 110 comprises the at least one venting element 132. In particular, the vial stopper 110 may comprise 2 to 10 venting elements 132, specifically 4 to 8 venting elements 132, more specifically 6 venting elements 132, as illustrated in FIGS. 1A to 1D. Further, an overall cross-sectional area of the vial stopper 110 in the intermediate region 130 through the at least one venting element 132 and perpendicular to an axis of the stopper body 114 may be 60% to 90% of a cross-sectional area of the mouth 120 of the vial 110, specifically 70% to 80% and more specifically 75%. This may specifically apply to embodiments of the vial stopper 110 comprising a central cavity 111 as shown in FIGS. 1A to 1D and/or to embodiments comprising a through hole 142 as shown in FIGS. 2A to 2D. In an alternative embodiment, the overall cross-sectional area of the vial stopper 110 in the intermediate region 130 through the at least one venting element 132 and perpendicular to an axis of the stopper body 114 may exceed 90% of the cross-sectional area of the mouth 120 of the vial 112. In particular, this may apply to embodiments of the vial stopper 110, wherein the vial stopper 110 does not comprise the central cavity 111 as described above and as for example shown in FIG. 1E. Specifically, an overall cross-sectional area of the vial stopper 110 in the intermediate region 130 through the at least one venting element 132 and perpendicular to an axis of the stopper body 114 may cover a range from 90% to 98% specifically 95% to 98% of the cross-sectional area of the mouth 120 of the vial 112. Accordingly, the at least one venting element 132, in particular the venting slot, may provide for a range from 2% to 10%, specifically 2% to 5% of the cross-sectional area of the mouth 120 of the vial 112 to be kept open when the stopper 110 is inserted into the mouth 120 of the vial 112 in the intermediate position 136 to allow the venting of the interior 134 of the vial 112.

In particular, the intermediate region 130 may have an essentially cylindrical shape 144 as can be seen, for example in FIGS. 1A to 1E and 2A to 2D. Furthermore, both the first 116 and the second sealing surface 124 may have cylindrical shapes 144 as shown in FIGS. 1A to 1E and 2A to 2D. Specifically, the first 116 and second sealing surfaces 124 may have identical diameters as depicted in Figures in 1B and 2B. In particular, the first 116 and second sealing surfaces 124 may have a larger diameter than the intermediate region 130 as can be seen, for example in FIG. 1B. Further, the stopper body 114 may be essentially rotationally symmetrical about an axis. Furthermore, the first 116 and second circumferential sealing surfaces 124 may both be shaped as surfaces of a circular cylinder ring about an axis, e.g., the central longitudinal axis, of the stopper body 114. The first 116 and second circumferential sealing surfaces 124 may, in particular, both have identical diameters.

An end 146 of the stopper 110 facing the vial 112 may be shaped as a closed flat circular surface. As shown, for example, in FIGS. 1B and 2B, the vial stopper 110 may further comprise at least one stopper head 148 at an outer end of the stopper body 114, for placing onto an outer rim 150 of the mouth 120 of the vial 112, the stopper head 148 having a larger diameter than the stopper body 114. In particular, the stopper body 114 and the stopper head 148 may be integrally formed as a single unitary piece. Further, the stopper body 114 may also be integrally formed. Specifically, the stopper body 114 may be fully or partially made of a plastic material. The stopper body 114 may, in particular, be fully or partially made of at least one material selected from the group consisting of butyl rubber, bromobutyl rubber and chlorobutyl rubber. Further, as illustrated in FIGS. 2A to 2D, the stopper body 114, in the intermediate region 130, may have a plurality of protrusions 152 on an outer surface 154, specifically a plurality of spherical protrusions 152 or partially spherical protrusions 152. The protrusions 152 may in particular contribute to a stable fixation and/or a stable positioning of the intermediate region 130 of the vial stopper 110 in the mouth 120 of the vial 112 and specifically in the neck of the vial 112. Further, the protrusions 152 may allow an additional gas exchange via the interstices surrounding the protrusions 152.

FIGS. 3A and 3B show a lyophilization vial kit 156 according to this disclosure comprising the vial stopper 110 as illustrated in FIGS. 2A to 2D (except the protrusions 152 which are not shown in FIGS. 3A and 3B), the lyophilization vial kit 156 being in an upside-down position. FIG. 3A depicts the lyophilization vial kit 156 in a front view with the vial 112 shown as transparent in order to illustrate the interaction between the vial 112 and the vial stopper 110. FIG. 3B shows the lyophilization vial kit 156 in a cross-sectional view with the vial stopper 110 rotated by 90° along the longitudinal axis as compared to FIG. 3A in order to illustrate a possible path of a liquid 159 may take for complete removal from the vial 112 by the retrieval device 143. The lyophilization vial kit 156 according to this disclosure comprises at least one vial stopper 110 according to this disclosure and at least one lyophilization vial 112. The lyophilization vial 156 has a mouth 120 dimensioned to interact with the vial stopper 110 in such a way that, in the first position 122 of the vial stopper 110 in the mouth 120, the first circumferential sealing surface 116 hermetically seals against the interior surface 118 of the mouth 120, wherein, in the second position 126 of the vial stopper 110 in the mouth 120, the second circumferential sealing surface 120 hermetically seals against an interior surface 118 of a mouth 120, wherein, in the intermediate position 136 in between the first 122 and second positions 126, the interior 134 of the vial 112 is vented via the at least one venting element 132.

Figure 3:
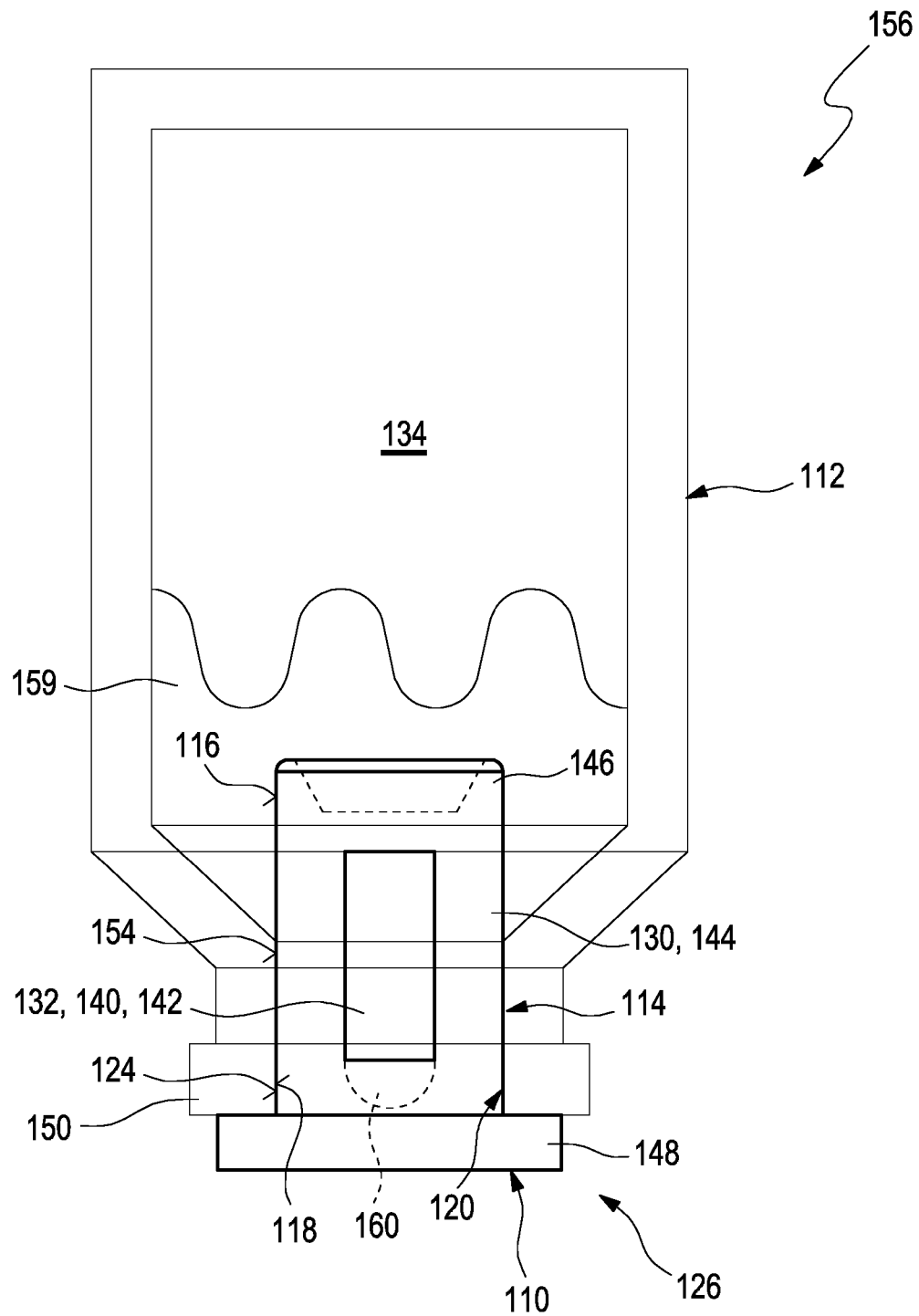
FIGS. 3A and 3B both show a lyophilization vial kit according to this disclosure comprising the vial stopper as illustrated in FIGS. 2A to 2D, the lyophilization vial kit being in an upside-down position in a front view (3A) and in a cross-sectional view with a retrieval device inserted into the vial (3B)
Figure 3:
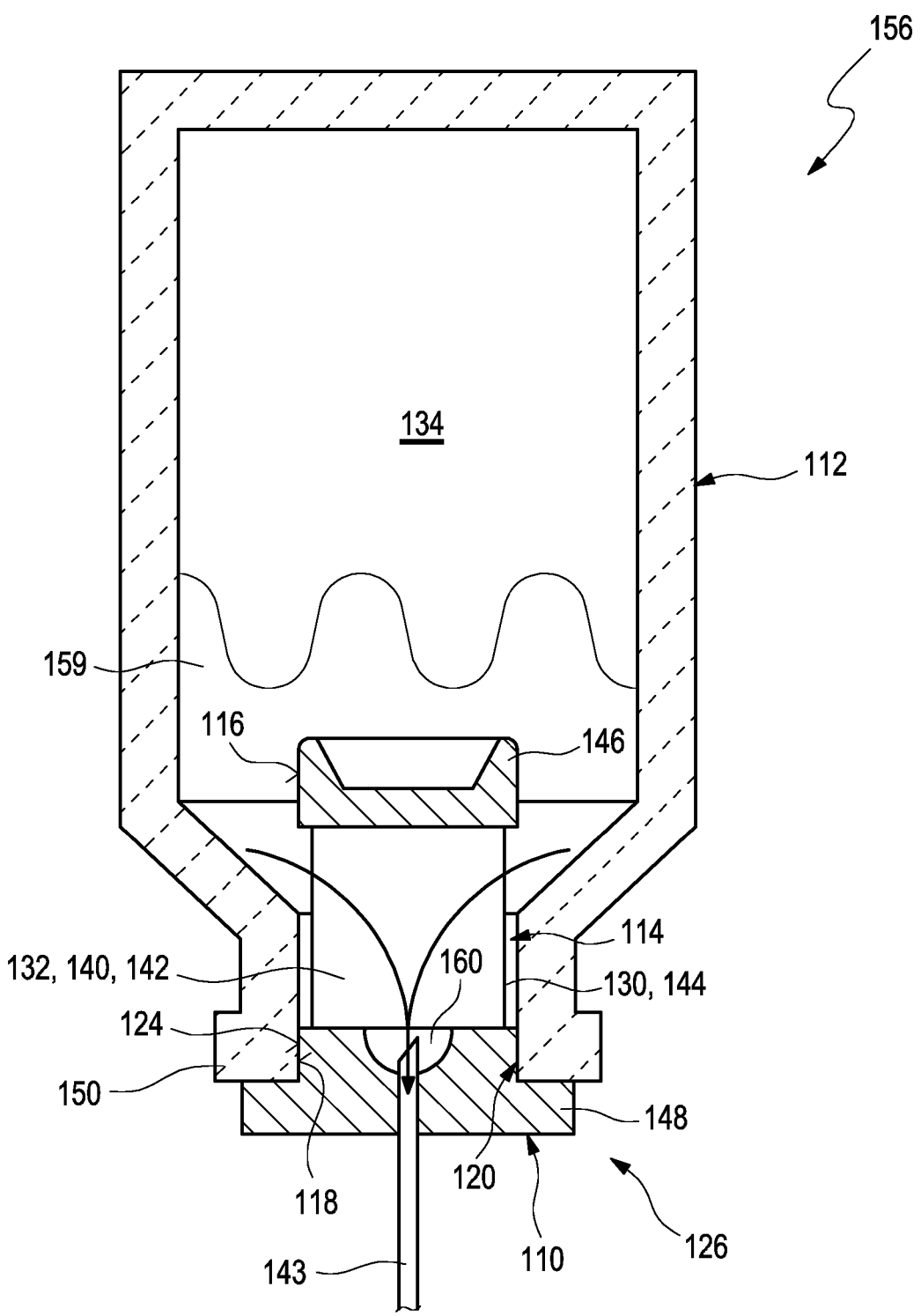

Specifically, the first position 122, the intermediate position 136 and the second position 126 may be positions of the vial stopper 110 relative to the vial 112, wherein the first position 122, the intermediate position 136 and the second position 126 may be sequentially reached, in the given order, when the vial stopper 110 is pushed into the mouth 120 of the vial 112. This is illustrated in FIGS. 4A to 4D. Accordingly, the second position 126, the intermediate position 136 and the first position 122 may be sequentially reached, in the given order, when the vial stopper is retracted from the mouth of the vial starting in the second position. The lyophilization vial kit 156 may further comprise a flange cap (not shown in the Figures), the flange cap being configured for being placed on top of the vial stopper 110 and flanging the vial stopper 110 against an outer rim 150 of the vial 112. Furthermore, the stopper 110 may be configured such that the liquid 159 contained in the lyophilization vial 112 may be completely removable from the vial 112 with the stopper 110 in the second position 126 by inserting the retrieval device 143 into the venting element 132 when the vial 112 is in an upside-down position, as shown in FIG. 3B. Such a configuration of the stopper 110 may be reached by a suitable arrangement, in particular a spatial arrangement, and/or a design of the at least one venting element 132 as described above. Thus, a vial stopper 110 as shown in FIGS. 2A to 2D and 3 having a venting element 132 comprising a through hole 142 may allow residual liquid 159 in the vial 112 to pass from the vial 112 into the venting element 132, in particular the through hole 142 (as indicated by the arrows in FIG. 3B), from where it may be removed by piercing the stopper 110 and inserting the retrieval device 143 shown in FIG. 3B into the venting element 132, in particular the through hole 142. The stopper 110 may specifically comprise an indentation 160 in communication with the venting element 132 as shown in FIGS. 2B, 2C and 3. The indentation 160 may be situated near the stopper head 148. The indentation 160 may further be configured to collect residual liquid 159 when the vial 112 is in an upside-down position and thus facilitate its removal by the retrieval element. The liquid 159 may, for instance, be a medical, pharmaceutical or biological product made from the lyophilisate by adding a solvent. The retrieval device 143 may specifically be selected from the group consisting of: a cannula; a tube; a drain tube; a mandrel; a syringe.

FIGS. 4A to 4D show selected steps of a lyophilization method 161 according to this disclosure by means of a cross-sectional view of the lyophilization vial kit 156 comprising the vial stopper 110 in an embodiment as depicted in FIGS. 2A to 2D. For the cross-sectional view of the vial stopper 110 as shown in FIGS. 4A to 4D the sectional plane cuts through the venting element 132 of vial stopper 110. In this view, the protrusions 152 are not apparitional. As shown in FIG. 4C, a length of the venting element 132 may exceed a height of the interior surface 118 of the mouth 120 of the vial 112. Thus, when the vial stopper 110 is placed in the intermediate position 136, the venting element 132 may protrude beyond the interior surface 118 of the mouth 120 of the vial 112 into both the interior 134 of the vial 112 and the outside of the vial 112 thereby establishing a fluid connection between the interior 134 of the vial 112 and the outside of the vial 112 in order to allow the exchange of a gaseous amount of the content or an ingredient of the content or the interior 134 of the vial 112 with the surroundings of the vial 112. In particular, the length of the venting element 132 may exceed the height of the interior surface 118 of the mouth 120 of the vial 112 by 2 mm to 10 mm, preferably by 4 mm, such that the venting element 132 may protrude, for example 1 mm to 5 mm, preferably 2 mm, into both the interior 134 of the vial 112 and the outside of the vial 112.

In a third aspect of this disclosure, a closure method for closing a lyophilization vial 112 is disclosed (not shown in the Figures). The method comprises the following steps, preferably in the designated order. An order other than the designated order may generally be possible. Further, one or several or all of the steps may be carried out repeatedly. Furthermore, two or more steps may be carried out simultaneously or in a fully or partially temporally overlapping fashion. The method may in addition to the steps specified below comprise further steps.

The closure method comprises the following steps:
a) providing at least one lyophilization vial kit 156 according to a lyophilization vial kit 156 of this disclosure;
b) pushing the vial stopper 110 into the mouth 120 of the vial 112 until the first position 122 is reached;
c) pushing the vial stopper 110 further into the mouth 120 of the vial 112 until the intermediate position 130 is reached, whereby the interior (134) of the vial (112) is vented; and
d) pushing the vial stopper 110 further into the mouth 120 of the vial 112 until the second position 126 is reached.

In particular after each of steps b), c) and d), the lyophilization vial kit 156 may remain in the respective position for at least 3 seconds. Further, after method step b) and before method step c), an optical inspection step of the content of the vial 112 to detect the presence of at least one solid component contained in the vial 112 may be performed. Specifically, the component may be a particle, e.g., glass particle, dust particle, metallic particle. Thus, the optical inspection step may, specifically, contribute to or be part of a quality control of the content of the vial 112. In particular, during the inspection step, the vial 112 may be rotated.

In a fourth aspect of this disclosure, the lyophilization method 161 as illustrated in FIGS. 4A to 4D is disclosed. The lyophilization method 161 comprises the following steps, preferably in the designated order. An order other than the designated order may generally be possible. Further, one or several or all of the steps may be carried out repeatedly. Furthermore, two or more steps may be carried out simultaneously or in a fully or partially temporally overlapping fashion. The method may in addition to the steps specified below comprise further steps.

The lyophilization method 161 comprises the following steps:
i) providing at least one lyophilization vial kit 156 according to a lyophilization vial kit 156 of this disclosure;
ii) filling at least one liquid 159 into the vial 112;
iii) pushing the vial stopper 110 into the mouth 120 of the vial 112 until the first position 122 is reached;
iv) pushing the vial stopper 110 further into the mouth 120 of the vial 112 until the intermediate position 136 is reached;
v) performing at least one lyophilization process, with the vial stopper 110 in the intermediate position 136, thereby converting the liquid 159 into at least one solid material, with at least one gaseous substance being vented from the interior 134 of the vial 112 through the venting element 132; and
vi) pushing the vial stopper 110 further into the mouth 120 of the vial 112 until the second position 126 is reached.

FIG. 4A shows the lyophilization vial 112 filled with liquid 159 as a result of steps i) and ii). In particular, with the vial stopper 110 in the first position 122, an optical inspection step may be performed. In particular, the optical inspection step may be an optical inspection step of at least one component contained in the vial 112. Specifically, the component may be a chemical substance and/or a particle, in particular, a contaminant. Thus, the optical inspection step may, specifically, contribute to or be part of a quality control of the content of the vial 112. In particular, during the inspection step, the vial may be rotated. FIG. 4B shows the lyophilization vial 112 with the stopper 110 in the first position 122 during rotation for optical inspection of the liquid 159. FIG. 4C illustrates the lyophilization process during which the vial stopper 110 is in the intermediate position 136 to allow the at least one gaseous substance to be vented from the interior 134 of the vial 112 through the venting element 132 as indicated in FIG. 4C by the arrows. FIG. 4D shows the vial 112 containing the lyophilisate 162 with the stopper 110 in the second position 126 as a result of step vi).

Figure 5:
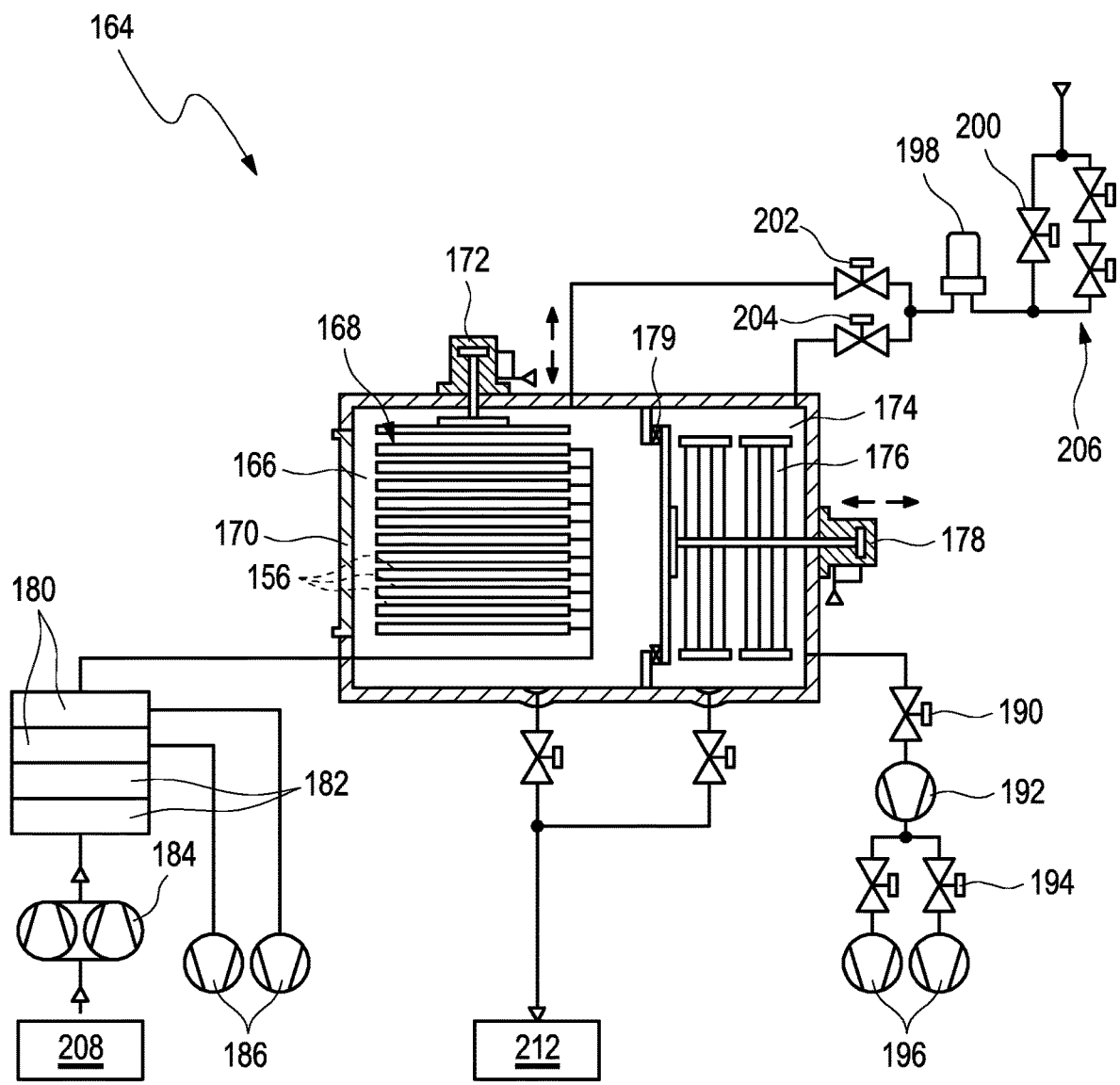
FIG. 5 shows a schematic overview of a lyophilization apparatus according to this disclosure.

In a fifth aspect of this disclosure, a lyophilization apparatus 164 as illustrated in FIG. 5 is disclosed. The lyophilization apparatus 164 comprises:
A) a plurality of lyophilization vial kits 156 according to a lyophilization vial kit 156 of this disclosure;
B) at least one filling device for filling at least one liquid 159 into the vials 112 of the lyophilization vial kits 156;
C) at least one pushing device for pushing the vial stoppers 110 of the vials 112 into the mouths 120 of the vials 112 in a stepwise fashion, thereby sequentially bringing the vial stoppers 110 into the first position 122, the intermediate position 136 and the second position 126.
D) a temperature application device; and
E) a pressure application device.

The lyophilization apparatus 164 may in particular comprise at least one cooling device for cooling the lyophilization vial kits 156. The lyophilization apparatus 164 may further comprise at least one optical inspection device (F) for optically inspecting the lyophilization vial kits 156. The lyophilization apparatus 164 may further comprise at least one controller (G) for controlling a lyophilization sequence, wherein, specifically, the controller may be configured for controlling the lyophilization apparatus 164 to perform the lyophilization method 161 according to a lyophilization method 161 of this disclosure. The lyophilization apparatus 164 may further comprise the following components as depicted in FIG. 5: a drying chamber 166, a set of shelves 168, a door of the drying chamber 170, hydraulic cylinder of set of shelves 172, ice condenser 174, tube packages 176 of a heat exchanger, a hydraulic cylinder 178 for opening and closing the intermediate valve 179, a cooling system 180 of a heat transfer medium, a heating system 182 of the heat transfer medium, heat transfer pumps 184, a refrigerating machine 186, a main vacuum valve for vacuum control 190, a Roots vacuum pump 192, a rotary vane vacuum pump 196, blocking valves 194 of the rotary vane vacuum pump 196, a germ-proof vent filter 198, a main ventilating valve 200, a ventilating valve 202 for the drying chamber 166, a ventilating valve 204 for the ice condenser 174, a dosage valve for vacuum control with an upstream needle valve 206. The lyophilization apparatus 164 may furthermore comprise the following components as also depicted in FIG. 5: further pumps 208, one or several compressors 210, a drain 212.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 vial stopper
111 central cavity
112 lyophilization vial
114 stopper body
116 first circumferential sealing surface
118 interior surface
120 mouth of the vial
122 first position
124 second circumferential sealing surface
126 second position
128 axial direction of the stopper body
130 intermediate region
132 venting element
134 interior of the lyophilization vial
136 intermediate position
138 venting slot
140 venting opening
142 through hole
143 retrieval device
144 essentially cylindrical shape
146 end of the stopper
148 stopper head
150 rim
152 protrusion
154 outer surface
156 lyophilization vial kit
158 upside-down position
159 liquid
160 indentation
161 lyophilization method
162 lyophilisate
164 lyophilization apparatus
166 drying chamber
168 set of shelves
170 door of drying chamber
172 hydraulic cylinder of set of shelves
174 ice condenser
176 tube packages
178 hydraulic cylinder
179 intermediate valve
180 cooling system of heat transfer medium
182 heating system of heat transfer medium
184 heat transfer pumps
186 refrigerating machine
190 main vacuum valve for vacuum control
192 Roots vacuum pump
194 blocking valves of rotary vane vacuum pump
196 rotary vane vacuum pump
198 germ-proof vent filter
200 main ventilating valve
202 ventilating valve for drying chamber
204 ventilating valve for ice condenser
206 dosage valve for vacuum control with upstream needle valve
208 further pumps
210 compressor
212 drain

What is claimed is:

1. A vial stopper for closure of a lyophilization vial, the vial stopper having a stopper body, the stopper body comprising:
   a first circumferential sealing surface configured for hermetically sealing against an interior surface of a mouth of the vial in a first position of the vial stopper;
   a second circumferential sealing surface for hermetically sealing against the interior surface of the mouth of the vial in a second position of the vial stopper, the second sealing surface being spaced apart from the first sealing surface in an axial direction of the stopper body; and
   an intermediate region axially positioned between the first and second sealing surfaces, the intermediate region having a vent configured for venting an interior of the vial in an intermediate position of the stopper between the first and second positions;
   wherein both the first and second sealing surfaces have cylindrical shapes and identical diameters, and wherein the first and second sealing surfaces have a larger diameter than the intermediate region.

2. The vial stopper according to claim 1, wherein the vent comprises at least one venting slot.

3. The vial stopper according to claim 2, wherein the venting slot extends in an axial direction of the stopper body.

4. The vial stopper according to claim 1, wherein the vent comprises at least one venting opening extending through the stopper body.

5. The vial stopper according to claim 1, wherein an overall cross-sectional area of the vial stopper in the intermediate region through the vent and perpendicular to an axis of the stopper body is 60% to 90% of a cross-sectional area of the mouth of the vial.

6. The vial stopper according to claim 1, wherein the mouth of the vial defines a cross-sectional area and the vent provides for a range from 2% to 10% of the cross-sectional area of the mouth of the vial to be kept open when the vial stopper is inserted into the mouth of the vial in the intermediate position.

7. A lyophilization vial kit, comprising:
   a lyophilization vial comprising a mouth having an interior surface;

a vial stopper having a stopper body, the stopper body comprising:
- a first circumferential sealing surface configured for hermetically sealing against the interior surface;
- a second circumferential sealing surface for hermetically sealing against the interior surface, the second sealing surface being spaced apart from the first sealing surface in an axial direction of the stopper body;
- an intermediate region axially positioned between the first and second sealing surfaces, the intermediate region having a vent configured for venting an interior of the vial in an intermediate position of the stopper;
- wherein both the first and second sealing surfaces have cylindrical shapes and identical diameters, and wherein the first and second sealing surfaces have a larger diameter than the intermediate region; and the mouth of the lyophilization vial being dimensioned to interact with the vial stopper such that, in a first position of the vial stopper in the mouth, the first circumferential sealing surface hermetically seals against the interior surface, and in a second position of the vial stopper in the mouth, the second circumferential sealing surface hermetically seals against the interior surface;

wherein the intermediate position is between the first and second positions and the interior of the vial is vented to outside of the vial via the vent when the vial stopper is in the intermediate position.

8. The lyophilization vial kit according to claim 7, wherein the first position, the intermediate position and the second position are positions of the vial stopper relative to the vial, wherein the first position, then the intermediate position and then the second position are sequentially reached when the vial stopper is pushed into the mouth of the vial.

9. A closure method for closing a lyophilization vial, the method comprising the following steps:
a) providing a vial stopper having first and second circumferential sealing surfaces and an intermediate region between the first and second sealing surfaces, the intermediate region having a vent;
b) providing a lyophilization vial comprising a mouth having an interior surface;
c) pushing the vial stopper into the mouth until a first position is reached in which the first circumferential sealing surface hermetically seals against the interior surface;
d) pushing the vial stopper further into the mouth of the vial until an intermediate position is reached, whereby the interior of the vial is vented via the vent; and
e) pushing the vial stopper further into the mouth of the vial until a second position is reached in which the second circumferential sealing surface hermetically seals against the interior surface.

10. The closure method according to claim 9, wherein, after method step c) and before method step d), an optical inspection step of at least one component contained in the vial is performed.

11. A lyophilization method, comprising:
a) providing a vial stopper having first and second circumferential sealing surfaces and an intermediate region between the first and second sealing surfaces, the intermediate region having a vent;
b) providing a lyophilization vial comprising a mouth having an interior surface;
c) adding at least one liquid into the vial;
d) pushing the vial stopper into the mouth of the vial until a first position is reached in which the first circumferential sealing surface hermetically seals against the interior surface;
e) pushing the vial stopper further into the mouth of the vial until an intermediate position is reached;
f) performing at least one lyophilization process with the vial stopper in the intermediate position, thereby converting at least some of the liquid into at least one solid material and venting at least one gaseous substance from an interior of the vial through the vent; and
g) pushing the vial stopper further into the mouth of the vial until a second position is reached in which the second circumferential sealing surface hermetically seals against the interior surface.

12. The lyophilization method according to claim 11, wherein, with the vial stopper in the first position, an optical inspection step is performed.

13. A lyophilization apparatus, comprising:
A) a plurality of lyophilization vial kits according to claim 7;
B) at least one filling device for adding at least one liquid into the vials of the lyophilization vial kits;
C) at least one pushing device for pushing the vial stoppers of the vials into the mouths of the vials in a stepwise fashion, thereby sequentially bringing the vial stoppers into the first position, the intermediate position and the second position;
D) a temperature applicator; and
E) a pressure applicator.

14. A lyophilization apparatus, comprising:
A) a plurality of lyophilization vial kits according to claim 7;
B) at least one filling device for adding at least one liquid into the vials of the lyophilization vial kits;
C) at least one pushing device for pushing the vial stoppers of the vials into the mouths of the vials in a stepwise fashion, thereby sequentially bringing the vial stoppers into the first position, the intermediate position and the second position;
D) a temperature applicator;
E) a pressure applicator; and
F) at least one optical inspection device for optically inspecting the lyophilization vial kits.

\* \* \* \* \*